United States Patent
Matsumoto et al.

(10) Patent No.: US 6,214,174 B1
(45) Date of Patent: *Apr. 10, 2001

(54) PURIFIER AND PURIFYING METHOD FOR POLYMERIZABLE ORGANIC COMPOUNDS

(75) Inventors: Hajime Matsumoto; Kazukiyo Arakawa, both of Himeji (JP)

(73) Assignee: Nippon Shokubai Co., Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/015,053

(22) Filed: Jan. 28, 1998

(30) Foreign Application Priority Data

Jan. 31, 1997 (JP) .................................................. 9-018261

(51) Int. Cl.[7] ............................... B01D 3/16; B01D 3/22; C07C 51/44
(52) U.S. Cl. ....................... 203/100; 202/158; 202/266; 203/8; 203/DIG. 21; 261/114.1; 261/114.4; 261/114.5; 562/600
(58) Field of Search .................... 202/158, 266, 202/183, 184; 261/109, 114.1, 114.4, 114.5; 422/256; 203/8, 42, 100, DIG. 21; 562/600; 159/DIG. 10, DIG. 41, DIG. 27, DIG. 28

(56) References Cited

U.S. PATENT DOCUMENTS

| | | |
|---|---|---|
| 3,717,553 | 2/1973 | Otsuki et al. . |
| 3,988,213 | 10/1976 | Yoshida et al. . |
| 4,028,443 * | 6/1977 | Livingston et al. ............... 261/114.5 |
| 4,051,206 * | 9/1977 | Bunas et al. .......................... 202/158 |
| 4,174,363 | 11/1979 | Bruckert . |
| 4,184,857 | 1/1980 | Iijima et al. . |
| 4,247,521 * | 1/1981 | Forte et al. ........................... 202/158 |
| 4,374,000 | 2/1983 | Abernathy et al. . |
| 4,405,449 * | 9/1983 | Trager ................................... 202/158 |
| 4,442,048 | 4/1984 | Abernathy et al. . |
| 4,744,929 * | 5/1988 | Robinson et al. ...................... 261/97 |
| 4,814,117 * | 3/1989 | Leva ....................................... 261/94 |
| 5,069,830 * | 12/1991 | Moore et al. .......................... 261/94 |

FOREIGN PATENT DOCUMENTS 63-41514 2/1988 (JP) .

* cited by examiner

Primary Examiner—Virginia Manoharan

(57) ABSTRACT

A distillation column is arranged so that a liquid hole which allows liquid containing a polymerizable organic compound to flow from on a tray supporting member downward is formed in a part of the tray supporting member, for example, a support ring, so that substantial retention of the liquid on the tray supporting member is avoided. Therefore, the liquid, such as crude acrylic acid, is allowed to smoothly flow down from on surfaces of a tray and the tray supporting member, thereby causing no substantial retention of the liquid. As a result, polymerization which tends to occur when the liquid is retained on the surfaces of the tray and the tray supporting member thereby being heated is effectively prevented, and the polymerizable organic compound is efficiently purified.

20 Claims, 3 Drawing Sheets

PURIFIER AND PURIFYING METHOD FOR POLYMERIZABLE ORGANIC COMPOUNDS

FIELD OF THE INVENTION

The present invention relates to a purifier and a purifying method for polymerizable organic compounds. Specifically, the present invention relates to a purifier and a purifying method with which polymerizable organic compounds (organic compounds which are easily polymerized) such as acrylic acid or methacrylic acid are efficiently purified by distillation or other processes, by effectively avoiding polymerization of the polymerizable organic compounds.

BACKGROUND OF THE INVENTION

Generally, purifying a polymerizable organic compound (an organic compound which is easily polymerized) such as acrylic acid or methacrylic acid, for example, by distilling it by the use of a distiller in the presence of a polymerization inhibitor, so as to transform it into products, is widely practiced in industrial fields.

When a polymerizable organic compound is distilled by the use of a conventional distiller, the polymerizable organic compound is substantially retained, in a liquid form, on a surface of a distiller constituent member (for example, a tray supporting member) of the distiller. Therefore, the retained liquid, that is, the polymerizable organic compound, is polymerized by, for example, heat application. As a result, a polymer is formed.

Therefore, in the distiller, a strainer is provided at a predetermined position so that the polymer is removed from the polymerized organic compound taken out of the distiller. Besides, the operation of the distiller is suspended at regular intervals for dismantling and checking of the distiller, so that the polymer adhering to inner surfaces of the distiller is washed away.

However, since a great amount of the polymer of the polymerizable organic compound is produced in the conventional distiller, cleaning of the strainer and the distiller has to be frequently conducted. In short, such a conventional distiller has a drawback in that efficient purification of a polymerizable organic compound is impossible.

Therefore, there has risen a demand for a purifier and a purifying method with which polymerization of the polymerizable organic compounds is effectively avoided when the polymerizable organic compounds are purified by distillation or other processes so that efficient purification is performed.

SUMMARY OF THE INVENTION

The inventors eagerly studied a purifier and a purifying method with which a polymerizable organic compound could be efficiently purified. As a result, it was found that by controlling substantial retention of a liquid containing a polymerizable organic compound on a purifier constituent member inside the purifier, polymerization of the polymerizable organic compound was effectively prevented, thereby enabling effective purification of the same. In addition, it was also found that to control the substantial retention of the liquid, a liquid passing part for allowing the liquid to flow from the constituent member downward may be provided in the purifier constituent member inside the purifier. The present invention was completed based on this finding.

The first object of the present invention is to pro vide a purifier with which polymerization of a polymerizable organic compound is effectively avoided when the polymerizable organic compound is purified by distillation or other processes so that efficient purification is performed.

To achieve the first object, a purifier of the present invention for purifying a polymerizable organic compound is characterized in comprising a liquid passing part provided in a purifier constituent member inside the purifier, the liquid passing part allowing liquid containing the polymerizable organic compound to flow from the constituent member downward, so as to avoid substantial retention of the liquid on the constituent member.

With the above arrangement, the liquid containing the polymerizable organic compound is allowed to smoothly flow from the constituent member downward through the liquid passing part, thereby causing no substantial retention of the liquid on the constituent member. As a result, polymerization which tends to occur when the liquid is retained on the surface of the constituent member thereby being heated is effectively prevented. Therefore, efficient purification of the liquid, that is, the polymerizable organic compound, is ensured.

The second object of the present invention is to provide a purifying method with which polymerization of a polymerizable organic compound is effectively avoided when the polymerizable organic compound is purified by distillation or other processes so that efficient purification is performed.

To achieve the second object, a purifying method of the present invention for purifying a polymerizable organic compound, which uses a purifier incorporating a constituent member in which a liquid passing part is formed, is characterized in comprising the step of allowing liquid containing the polymerizable organic compound to flow from the constituent member downward through the liquid passing part, so as to avoid substantial retention of the liquid on the constituent member.

By the aforementioned method, the polymerization which tends to occur when the liquid is retained on the constituent member thereby being heated can be effectively avoided, and as a result the liquid, that is, the polymerizable organic compound, can be efficiently purified.

For a fuller understanding of the nature and advantages of the invention, reference should be made to the ensuing detailed description taken in conjunction with the accompanying drawings.

DESCRIPTION OF THE PREFERRED EMBODIMENTS

Polymerizable organic compounds in the present invention are organic compounds which are characterized in that they are easily polymerized by, for example, heat application. Examples of such polymerizable organic compounds include: unsaturated carboxylic acids, such as acrylic acid, and methacrylic acid (hereinafter these two are generically called (meth) acrylic acid); alkyl esters of the unsaturated carboxylic acids, such as methyl (meth)acrylate, ethyl (meth)acrylate, propyl (meth)acrylate, butyl (meth)acrylate, 2-ethylhexyl (meth)acrylate, and cyclohexyl (meth)acrylate; hydroxylic alkyl esters of the unsaturated carboxylic acids, such as hydroxyethyl (meth)acrylate, and hydroxypropyl (meth)acrylate; dialkylaminoalkyl esters of the unsaturated carboxylic acids, such as dimethylaminoethyl (meth) acrylate, and diethylaminoethyl (meth)acrylate; alkoxyalkyl esters of the unsaturated carboxylic acids such as methoxyethyl (meth)acrylate, and ethoxyethyl (meth)acrylate; glycidyl esters of the unsaturated carboxylic acids; vinyl-group-containing compounds, such as acrylonitril, styrene, and vinyl acetate; and diolefin compounds, such as butadiene, isoprene, and chloroprene. But, no specific one among the polymerizable organic compounds is particularly preferred in the present invention.

Purification in the present invention refers to (1) distillation, (2) diffusion, or (3) absorption of the polymerizable organic compound. Here, distillation refers to separation of a liquid-form mixture into components by utilizing differences between vapor pressures of the components. As concrete methods of distillation, there are simple distillation, multi-stage distillation, azeotropic distillation, steam distillation, and the like, and no specific one is particularly preferred in the present invention. Diffusion refers to expelling (removing) at least one component constituting a solution (dissolved in a solvent) out of the solution by bringing the solution into contact with a gas which does not contain the component. Absorption refers to causing at least one component of a gaseous mixture to be dissolved (absorbed) in a solvent.

The following description will explain a purifier and a purifying method of the present invention by taking as an example a case where acrylic acid is selected as the polymerizable organic compound and it is purified by distillation, while referring to FIGS. 1 through 7.

Figure 1:
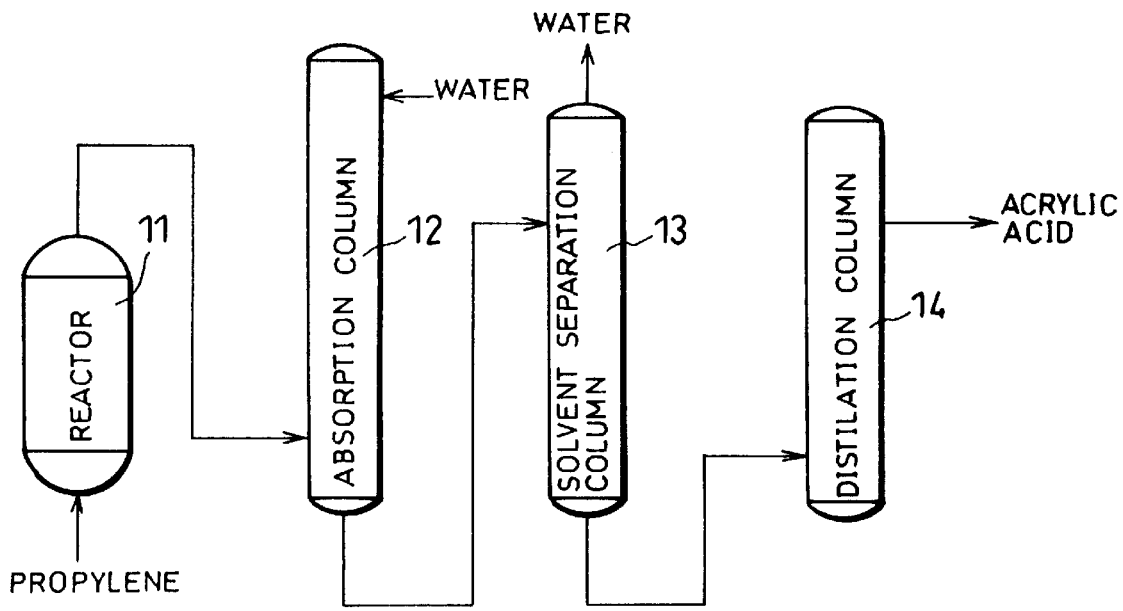
FIG. 1 is a block diagram illustrating a schematic arrangement of a producing device of a polymerizable organic compound which is equipped with a distillation column as a purifier of the present invention.

The acrylic acid is obtained by vapor phase oxidization of a material such as propylene in an oxygen-containing gas in the presence of an oxidation catalyst. As shown in FIG. 1, a gas containing acrylic acid is produced in a reactor 11, and is introduced into the vicinity of a bottom of an absorption column 12. In the absorption column 12, the gas thus produced through reaction is cooled with the use of water (solvent) introduced through a column top, and it is condensed to an acrylic acid aqueous solution. Then, light boiling point components are removed from the acrylic acid aqueous solution. The acrylic acid aqueous solution from which light boiling point components have been removed is taken out from the bottom of the absorption column 12, and is introduced into the vicinity of a middle stage of a solvent separation column 13. In the solvent separation column 13, crude acrylic acid is separated from the acrylic acid aqueous solution. The crude acrylic acid is taken out from the bottom of the solvent separation column 13, and is introduced into the vicinity of a bottom of a distillation column 14. Water as the solvent is taken out from the top of the solvent separation column 13. In the distillation column 14 as a purifier, the crude acrylic acid is distilled. The acrylic acid purified by distillation is taken out of the distillation column 14, thereby becoming products. Note that operational conditions for the reactor 11, the absorption column 12, the solvent separation column 13, and the distillation column 14, that is, operational conditions for the producing device, are not specifically limited.

The distillation column 14 is, for example, a multi-stage distillation column in which a plurality of trays are provided. The trays are fixed at predetermined positions inside the distillation column, supported by a tray supporting member.

Figure 2:
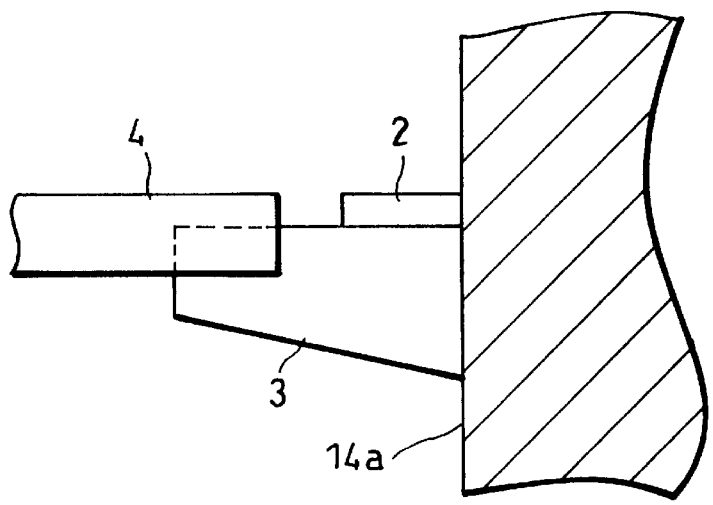
FIG. 2 is a side view illustrating an arrangement of principal parts of a tray supporting member as a distillation column constituent member inside the distillation column.
Figure 3:
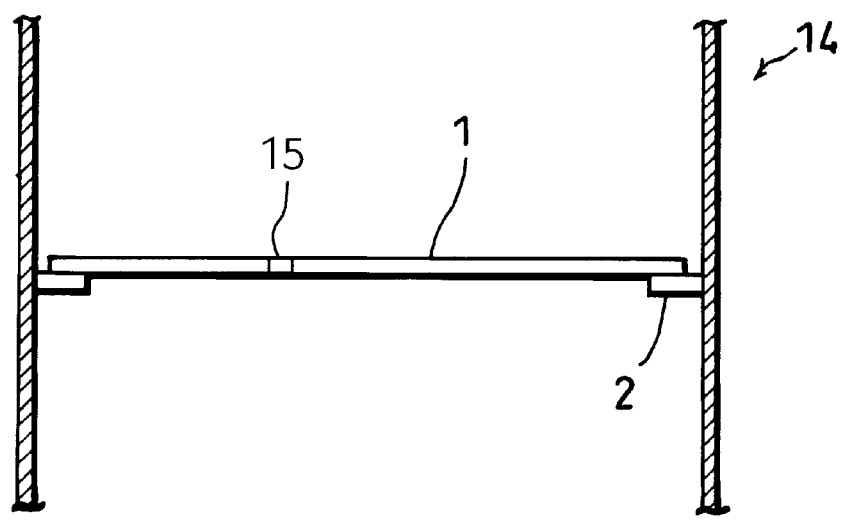
FIG. 3 is a cross-sectional view illustrating an arrangement of principal parts inside the distillation column.
Figure 4:
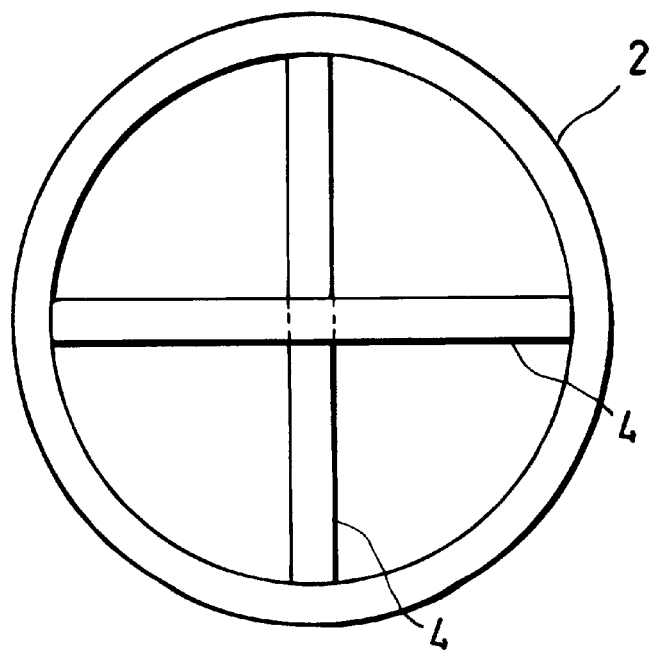
FIG. 4 is a plan view illustrating a principal part arrangement of the tray supporting member.

As shown in FIGS. 2 through 5, the tray supporting member as a constituent member inside the purifier is composed of a support ring 2, a lug 3, support beams 4, a washer 5, a clamp 6, a bolt 7a, and a nut 7b. As shown in FIG. 2, the lug 3 is fixed on an inside wall 14a of the distillation column, by bolting or welding, for example. As illustrated by FIGS. 2 and 3, the support ring 2 in a ring form is fixed on the lug 3 by, for example, bolting or welding so that the tray 1 is held thereon. As shown in FIGS. 2 and 4, the support beams 4 in a bar form are fixed on the lug 3 by, for example, bolting or welding, so that they orthogonally cross each other. The support beams 4 have bolt holes (not shown), so that the tray 1 is fixed thereon by bolting. Thus, the support beams 4 are provided under the tray 1 so as to support it, thereby contributing to improvement of mechanical strength of the tray 1.

Note that the tray 1 is usually composed of a plurality of parts combined with each other, but for purposes of illustration, an integrally-formed one is shown in the drawings. Besides, the number of the support beams 4 may be appropriately determined, depending on a size and a weight of the tray 1, and it is not specifically limited. However, the number is preferably plural.

Figure 5:
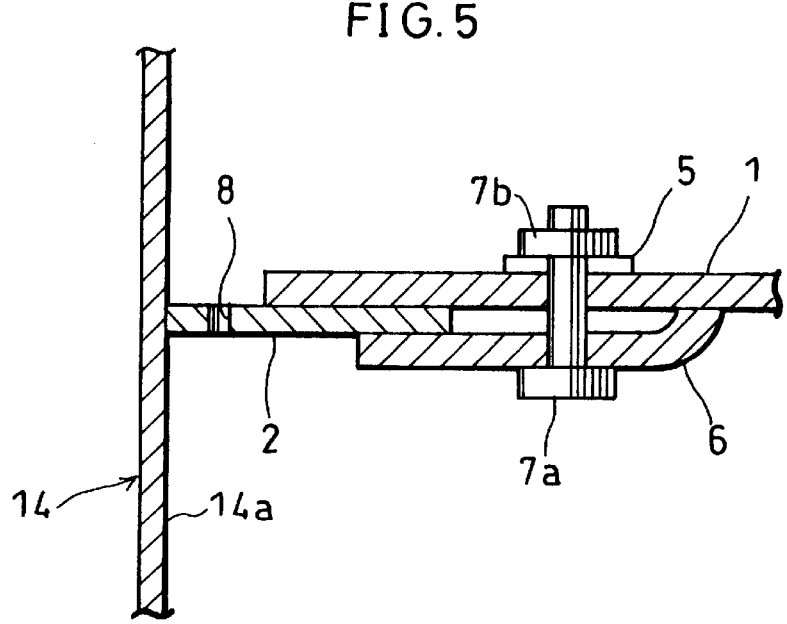
FIG. 5 is a cross-sectional view illustrating the principal part arrangement of the tray supporting member.

As illustrated in FIG. 5, the tray 1 is fixed on the support ring 2 by the washer 5, the clamp 6, the bolt 7a, and the nut 7b. More specifically, the tray 1 is fixed to the support ring 2 in the following manner: in a state where the support ring 2 is sandwiched between the tray 1 and the clamp 6, the bolt 7a pierces through a hole of the clamp 6, a hole of the tray 1, and the washer 5 from below in this order, then, the bolt 7a is fixed with the nut 7b.

A liquid passing part which allows liquid such as the crude acrylic acid to smoothly flow down therethrough from surfaces of the tray 1 and the tray supporting member is provided in at least one part of the tray supporting member, that is, at least one selected from the group consisting of the support ring 2, the lug 3, the support beams 4, the washer 5, the clamp 6, the bolt 7a, and the nut 7b, so that the liquid would not be substantially retained on the surfaces of the tray 1 and the tray supporting member. To be more specific, the liquid passing part is formed in a horizontal portion (a portion which is substantially horizontal when being set inside the distillation column 14) of at least one among the support ring 2, the lug 3, the support beams 4, the washer 5, the clamp 6, the bolt 7a, and the nut 7b, so that the liquid passing part vertically pierces the horizontal portion.

For example, in the case where the liquid passing part is formed in the support ring 2, a liquid hole 8 as the liquid passing part may be provided in a portion of the support ring 2 in the vicinity of the inside wall 14a of the distillation column, as illustrated in FIG. 5. In other words, the liquid hole 8 may be formed at least at a position such that the tray 1 does not cover the whole part of the liquid hole 8. Note that in the case where the liquid hole 8 is formed at a position such that the whole part of the liquid hole 8 is covered by the tray 1, a hole with a size substantially equal to the size of the liquid hole 8 may be formed in the tray 1 at a position corresponding to the liquid hole 8. By doing so, the liquid is allowed to smoothly flow down from on surfaces of the tray 1 and the tray supporting member.

The size and the number of the liquid hole 8 to be provided in the support ring 2 are not particularly limited, and may be appropriately determined depending on the size of the support ring 2 or the like. To be more specific, the size and the number of the liquid hole 8 may be set in ranges such that the liquid smoothly flows from on the tray supporting member downward while a mechanical strength required of the support ring 2 for holding the tray 1 is not impaired. It should be noted that it is not preferable to form the liquid hole 8 extremely large, since in such a case the liquid flows down without sufficient gas-liquid contact on the tray 1, thereby deteriorating distillation performance of the distillation column 14. Besides, it is not preferable as well to form the liquid hole 8 extremely small, since in such a case the liquid is not allowed to smoothly flow down, thereby making it impossible to effectively prevent polymerization.

A shape of the liquid hole 8 (a shape of an aperture) is not particularly limited, and the liquid hole 8 may have various shapes such as a circular shape, a semi-circular shape, an oval shape, or a polygonal shape. But the circular shape or the semi-circular shape is preferable.

Figure 7:
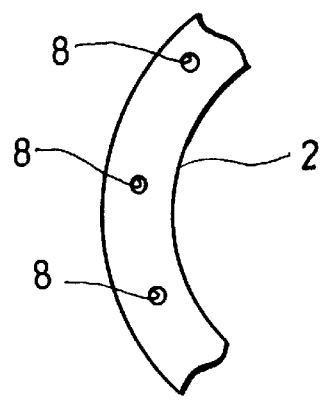
FIG. 7 is a plan view illustrating still another principal part arrangement of the tray supporting member.

In the case where a plurality of the liquid holes 8 are formed as illustrated in FIG. 7, intervals (pitches) of the liquid holes 8 are not specifically limited, and they may be appropriately determined depending on the size of the support ring 2, the size and the number of the liquid holes 8, and the like. More specifically, for example, the liquid holes 8 may be arranged at intervals such that the liquid smoothly flows from on the tray supporting member downward while a mechanical strength required of the support ring 2 for holding the tray 1 is not impaired.

To be more concrete, for example, in the case where the width of the support ring 2 in a ring shape is 20 mm to 100 mm, the liquid holes 8 with a diameter of 3 mm to 30 mm, or preferably 5 mm to 20 mm, or more preferably 6 mm to 15 mm, may be arranged at intervals of 25 mm to 500 mm, or preferably 50 mm to 400 mm, or more preferably 100 mm to 200 mm.

Figure 6:
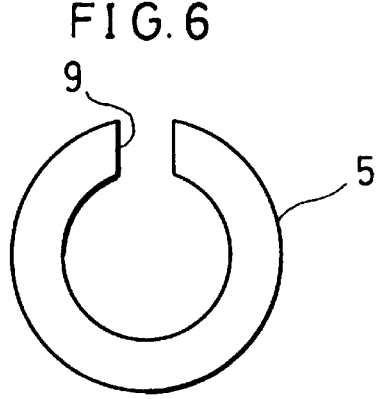
FIG. 6 is a plan view illustrating another principal part arrangement of the tray supporting member.

Furthermore, in the case where the liquid passing part is formed in the washer 5, a cutout 9 as the liquid passing part may be formed in the washer 5, as illustrated in FIG. 6. A size of the cutout 9 as the liquid passing part to be formed in the washer 5 is not particularly limited, and it may be set so that the liquid smoothly flows from on the tray supporting member downward while a function of the washer 5 is not impaired. By doing so, the liquid can be allowed to smoothly flow down from on surfaces of the tray 1 and the tray supporting member.

Furthermore, in the case where the liquid passing part is formed, for example, in the support beams 4, a liquid hole (not shown) as the liquid passing parts may be formed in the support beams 4. The liquid hole of the support beams 4 may be formed at least at a position such that the tray 1 does not cover the whole part of the liquid hole. Note that in the case where the liquid hole is formed at a position such that the whole part of the liquid hole is covered by the tray 1, a hole with a size substantially equal to the size of the liquid hole may be formed in the tray 1 at a position corresponding to the liquid hole. By doing so, the liquid can be allowed to smoothly flow down from on surfaces of the tray 1 and the tray supporting member.

The size and the number of the liquid hole to be provided in the support beams 4 are not particularly limited, and may be appropriately determined depending on the size of the support beams 4 or the like. To be more specific, the size and the number of the liquid hole may be set in ranges such that the liquid smoothly flows from on the tray supporting member downward while a mechanical strength required of the support beams 4 for holding the tray 1 is not impaired.

It should be noted that it is not preferable to form the liquid hole extremely large, since in such a case the liquid flows down without sufficient gas-liquid contact on the tray 1, thereby deteriorating distillation performance of the distillation column 14. Besides, it is not preferable as well to form the liquid hole extremely small, since in such a case the liquid is not allowed to smoothly flow down, thereby making it impossible to effectively prevent polymerization.

A shape of the liquid hole (a shape of an aperture) is not particularly limited, and the liquid hole may have various shapes such as a circular shape, a semi-circular shape, an oval shape, or a polygonal shape. But, the circular shape or the semi-circular shape is preferable. In the case where a plurality of the liquid holes are formed, intervals (pitches) of the liquid holes are not specifically limited, and they may be appropriately determined depending on the size of the support beams 4, the size and the number of the liquid holes, and the like. More specifically, for example, the liquid holes may be arranged at intervals such that the liquid smoothly flows from on the tray supporting member downward while a mechanical strength required of the support beams 4 for supporting the tray 1 is not impaired.

To be more concrete, for example, in the case where the width of the support beams 4 in a bar shape is 30 mm to 100 mm and holes for bolts for fixing the tray 1 which have a diameter of 8 mm to 30 mm each are arranged at 50 mm to 500 mm intervals, the liquid holes with a diameter of 3 mm to 30 mm, or preferably 5 mm to 20 mm, or more preferably 6 mm to 15 mm, may be arranged, desirably along a center line of the support beam 4 running in the lengthwise direction thereof, at 50 mm to 500 mm intervals, or preferably 100 mm to 400 mm intervals, or more preferably 100 mm to 200 mm intervals.

Furthermore, to form the liquid passing part in the lug 3, a liquid hole (not shown) as the liquid passing part may be formed in the lug 3. Specifically, the liquid hole in the lug 3 may have a size substantially equal to the liquid hole (8) formed in the support ring 2 and/or the support beams 4, and may be provided at a position corresponding to the liquid hole (8). By doing so, the liquid can be allowed to smoothly flow down from on surfaces of the tray 1 and the tray supporting member.

It should be noted that the liquid passing part may be formed in at least one part of the tray supporting member, that is, in at least one selected from the group consisting of the support ring 2, the lug 3, the support beams 4, the washer 5, the clamp 6, the bolt 7a, and the nut 7b, so that the liquid smoothly flows down from on the surfaces of the tray 1 and the tray supporting member.

Thus, by using the aforementioned producing device in predetermined desired operative conditions, the polymerizable organic compounds can be produced. By doing so, the polymerizable organic compounds can be efficiently purified, with polymerization of the polymerizable organic compounds effectively prevented. The operative conditions for the producing device, particularly the operative conditions for the distillation column 14, are not particularly limited, and may be appropriately determined, depending on properties of the polymerizable organic compounds, types of impurities contained in the liquid, and the like.

As described above, in the distillation column 14 as the purifier of the present invention, the liquid passing part which allows the liquid to flow down from on the tray supporting member is formed in the tray supporting member as the constituent member of the distillation column 14, so as to avoid substantial retention of the liquid containing the polymerizable organic compounds on the tray supporting member. In addition, as described above, the distillation column 14 is arranged so that in a horizontal portion of the tray supporting member, the liquid passing part (liquid hole and/or cutout) is formed so as to pierce the horizontal portion in a vertical direction. Moreover, as described above, in the distillation column 14, the tray supporting member is composed of at least the support ring, the lug, the support beams, the washer, and the clamp. Further, the liquid passing part is formed in at least one member selected from the group consisting of the support ring, the lug, the support beams, the washer, and the clamp.

With the above arrangement, liquid such as crude acrylic acid or the like is allowed to smoothly flow down from on the surfaces of tray 1 and the tray supporting member through the liquid passing part. Therefore, the liquid is by no means substantially retained on the surfaces of the tray 1 and the tray supporting member. As a result, the polymerization, which tends to occur when on the surfaces of the tray 1 and the tray supporting member the liquid is retained and heated, can be effectively avoided, thereby ensuring efficient purification of the liquid, that is, the polymerizable organic compound.

As described above, the purifier of the present invention for purifying a polymerizable organic compound is characterized in comprising an arrangement for purifying a polymerizable organic compound without causing substantial retention of the liquid on said constituent member.

Furthermore, the purifying method of the present invention for purifying a polymerizable organic compound, which utilizes a purifier incorporating a constituent member in which a liquid passing part is formed, comprises the step of allowing liquid containing the polymerizable organic compound to flow down from on the constituent member through the liquid passing part, so as to avoid substantial retention of the liquid on the constituent member.

By the above method, the polymerization which tends to occur when the liquid is retained on the constituent member and is heated can be effectively prevented. Therefore, the liquid, that is, the polymerizable organic compound, can be efficiently purified.

Note that in the above description, a case where the acrylic acid is selected as the polymerizable organic compound and purification is carried out by distilling the acrylic acid is taken as example, but the purifier and the purifying method of the present invention are not limited to the above example case. Besides, in the above description, a case where the distillation column 14 which is a multi-stage distillation column is used as the purifier and the liquid passing part is formed in the tray supporting member is taken as example, but in the case where a packed column, for example, is used as the purifier, the liquid passing part may be formed in a packing material holding member as a constituent member inside the purifier. By doing so, like in the case where a multi-stage distillation column is used, the polymerization of the polymerizable organic compound is effectively avoided, thereby ensuring efficient purification of the same.

The following description will explain the present invention in more detail by exhibiting examples, but these examples are not intended to impose any specific limitation on the present invention.

EXAMPLE 1

A reactive gas containing acrylic acid, which had been obtained as a result of contact vapor-phase oxidization of propylene, was brought into contact with water, and an acrylic acid aqueous solution was obtained. Then, crude acrylic acid was obtained by separating water from the acrylic acid aqueous solution. The crude acrylic acid was distilled for purification, and as a result acrylic acid as a polymerizable organic compound was obtained.

A multi-stage distillation column, made of stainless steel (SUS316) and having an inner diameter of 1800 mm, was used as a distillation column (purifier). Inside the distillation column, 50 sieve trays made of stainless steel (SUS316) were installed. Therefore, the distillation column had 50 stages. The sieve trays were arranged as described above, that is, so that they were fixed inside the distillation column by the use of the tray supporting members. A support ring as one part of each tray supporting member had a width of 50 mm, and 28 liquid holes in a circular shape with a diameter of 6 mm each were formed at 200 mm intervals in each support ring. In a lug as one part of the tray supporting member as well, liquid holes with a size substantially equal to the size of the liquid holes in the support ring were formed at positions corresponding to the above liquid holes in the support ring. In addition, a strainer for removing polymers from the acrylic acid to be taken out from the distillation column was installed at a predetermined position in the distillation column.

The distillation column thus arranged was continuously operated at a temperature of 63° C. and a pressure of 35 mmHg at the column top, at a temperature of 100° C. and a pressure of 120 mmHg at the column bottom, and at a reflux ratio of 1.4. Hydroquinone was used as a polymerization inhibitor. The hydroquinone was added to a refluxed liquid so that a ratio thereof to steam in the distillation column was 50 ppm. Further, oxygen-containing gas was continuously supplied at a predetermined rate, into the distillation column through the column bottom.

Then, in the aforementioned operational conditions, distillation of the crude acrylic acid was continued about one month. Thereafter, the distillation column was dismantled and checked, to measure an amount of polymer adhering to the sieve trays. The frequency (cleaning frequency) of cleaning of the strainer so as to remove the polymer therefrom while the continuous distillation was carried out was also checked. The results are shown in Table 1 below.

EXAMPLE 2

The continuous distillation with respect to the crude acrylic acid was carried out about one month in the same operative conditions as those in Example 1, except that the number of the liquid holes was increased as compared with Example 1 and the 200 mm intervals were changed to 100 mm intervals. Then, an amount of produced polymer was measured, while the strainer cleaning frequency was checked. The result is shown in Table 1 below.

COMPARATIVE EXAMPLE 1

The continuous distillation with respect to the crude acrylic acid was carried out about one month in the same operative conditions as those in Example 1, except that no liquid hole was formed in the support ring. Then, the amount of produced polymer was measured, while the strainer cleaning frequency was checked. The result is shown in Table 1 below.

TABLE 1

| | LIQUID HOLES | | AMOUNT OF PRODUCED POLYMER (kg) | STRAINER CLEANING FREQUENCY |
| --- | --- | --- | --- | --- |
| | DIAMETER (mm) | INTERVAL (mm) | | |
| EXAMPLE 1 | 6 | 200 | 3 | ONCE/7 DAYS |
| EXAMPLE 2 | 6 | 100 | 2 | ONCE/7 DAYS |
| COMPARATIVE EXAMPLE 1 | — | — | 10 | ONCE/1 DAY |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A purifier for purifying a polymerizable organic compound, said purifier comprising:
   a tray column or a packed column;

a tray for capturing purified liquid formed during distillation, diffusion or absorption of the polymerizable organic compound occurring on the tray, wherein the tray includes a drain through which liquids captured on the tray flow down through die tray;

a tray supporting member in said column on which said tray is supported;

a plurality of liquid passing apertures are provided in the tray supporting member inside said purifier, said liquid passing aperture allowing liquid containing the polymerizable organic compound to flow down through said tray supporting member, so as to avoid substantial retention of the liquid on said tray supporting member, and the liquid passing apertures each have an aperture diameter of 3 mm to 30 mm each, and are spaced at 25 mm to 500 mm intervals in the tray supporting member.

2. The purifier as set forth in claim 1, wherein said liquid passing apertures are formed in a portion of said tray supporting member which are horizontal when said tray supporting member is fixed inside said purifier, so that said liquid passing apertures pierce the horizontal portion in a vertical direction.

3. The purifier as set forth in claim 2, wherein said liquid passing apertures are in at least one member selected from the group consisting of a support ring, a lug, a support beam, a washer, and a clamp.

4. The purifier as set forth in claim 1, wherein the tray supporting member is selected from a group consisting of a support ring, a lug, a support beam, a washer, and a clamp.

5. The purifier as set forth in claim 4, wherein said liquid passing apertures are formed in the support ring.

6. The purifier as set forth in claim 1, wherein the polymerizable organic compound is an unsaturated carboxylic acid or an ester of the same.

7. The purifier as set forth in claim 1, wherein the polymerizable organic compound is acrylic acid.

8. The purifier as set forth in claim 1, wherein said liquid passing apertures also avoids heat-induced polymerization of the polymerizable organic compound in said purifier.

9. The purifier as set forth in claim 1, wherein said tray is provided so as to substantially cover a cross section of said column, and an entirety of said tray is arranged so as to pass vapor and liquid therethrough.

10. The purifier as set forth in claim 9, wherein said tray is a sieve tray.

11. The purifier as set forth in claim 1, wherein said tray is detachably supported by said tray supporting member disposed under said tray.

12. The purifier as set forth in claim 11, wherein said tray supporting member is a support ring and a lug provided along an inside wall of said column.

13. The purifier as set forth in claim 1, wherein:

said tray supporting member includes a support beam having a bolt hole; and said tray is fixed to the support beam by bolting utilizing the bolt hole.

14. The purifier as set forth in claim 13, wherein said liquid passing apertures are formed in the support beam, at different positions from that of the bolt hole.

15. The purifier as set forth in claim 1, wherein said tray is supported in a state in which said tray supporting member is sandwiched between said tray and a clamp.

16. The purifier as set forth in claim 15, wherein said tray is held by bolting utilizing bolt holes formed in said tray supporting member and the clamp.

17. A purifier for purifying a polymerizable organic compound, said purifier comprising:

a tray column or a packed column:

a tray for condensing and capturing purified liquid formed during distillation, diffusion or absorption of the polymerizable organic compound occuring on the tray, wherein the tray includes a drain through which liquids captured on the tray flow down through the tray;

a tray supporting member in said column on which said tray is supported;

a plurality of liquid passing apertures are provided in the tray supporting member inside said purifier, said liquid passing aperture allowing liquid containing the polymerizable organic compound to flow down through said tray supporting member, so as to avoid substantial retention of the liquid on said tray supporting member, and wherein the plurality of said liquid passing apertures are each formed with an aperture diameter of 3 mm to 30 mm each, and are spaced at intervals of 50 mm to 500 mm in said tray supporting member.

18. A purifying method for purifying a polymerizable organic compound by the use of a purifier, the purifier having a tray column or a packed column, and incorporating a liquid capturing member and a liquid capturing support member in which a plurality of liquid passing apertures are formed, said purifying method comprising the steps of:

(a) collecting a purified liquid polymerizable organic compound on the liquid capturing member in the purifier during distillation, diffusion or adsorption of the compound;

(b) draining collected and purified liquid in a continual flow down through the liquid capturing member, such that the liquid does not become stagnant on the liquid capturing member;

(c) supporting the liquid capturing member in the purifier with the liquid capturing support member, and (d) draining liquid containing the polymerizable organic compound on the liquid capturing member through the liquid passing apertures in the support member, so as to avoid substantial retention of the liquid on the liquid capturing support member, wherein the plurality of said liquid passing apertures each have an aperture diameter of 3 mm to 30 mm each, and the apertures are spaced at intervals of 25 mm to 500 mm in the tray supporting member.

19. The purifying method as set forth in claim 18, wherein the polymerizable organic compound is an unsaturated carboxylic acid or an ester of the same.

20. The purifying method as set forth in claim 18, wherein the polymerizable organic compound is acrylic acid.

* * * * *

UNITED STATES PATENT AND TRADEMARK OFFICE
CERTIFICATE OF CORRECTION

PATENT NO. : 6,214,174 B1
DATED : April 10, 2001
INVENTOR(S) : Matsumoto et al.

Page 1 of 1

It is certified that error appears in the above-identified patent and that said Letters Patent is hereby corrected as shown below:

<u>Column 9,</u>
Line 5, "die tray" should read -- the tray --.

Signed and Sealed this

Twenty-eighth Day of August, 2001

*Attest:*

*Nicholas P. Godici*

NICHOLAS P. GODICI
*Attesting Officer*   *Acting Director of the United States Patent and Trademark Office*